United States Patent [19]

Wong

[11] Patent Number: 5,516,665

[45] Date of Patent: May 14, 1996

[54] N-ACETYLGALACTOSAMINYL OR N-ACETYLGLUCOSAMINYL TRANSFER USING N-ACETYLGLUCOSAMINYL-1-PHOSPHATE OR N-ACETYLGALACTOSAMINYL-1-PHOSPHATE AS PRECURSOR AND GLYCOSYL-NUCLEOTIDE REGENERATION

[75] Inventor: Chi-Huey Wong, Rancho Santa Fe, Calif.

[73] Assignee: The Scripps Research Institute, La Jolla, Calif.

[21] Appl. No.: 120,179

[22] Filed: Sep. 13, 1993

[51] Int. Cl.[6] .......................... C12P 19/18; C12P 19/00; C12P 19/30; C12P 19/24
[52] U.S. Cl. ................. 435/97; 435/72; 435/89; 435/94; 435/100; 435/101
[58] Field of Search .................. 435/72, 89, 94, 435/97, 100, 101

[56] References Cited

U.S. PATENT DOCUMENTS

| | | | |
|---|---|---|---|
| 4,569,909 | 2/1986 | Seno et al. ...................... | 435/89 |
| 5,068,191 | 11/1991 | Clausen et al. ................. | 435/193 |
| 5,180,674 | 1/1993 | Roth ................................ | 435/288 |
| 5,246,840 | 9/1993 | Nilsson .......................... | 435/101 |
| 5,264,352 | 11/1993 | Thiem et al. .................... | 435/97 |

OTHER PUBLICATIONS

Pure & Appl. Chem. 65(4): pp. 803–808 (1993), Wong et al.
J. Am. Chem. Soc. 113(16): pp. 6300–6302, (1991), Ichikawa et al.
J. Org. Chem. 47(27): pp. 5416–5418 (1982), Wong et al.

*Primary Examiner*—Michael G. Wityshyn
*Assistant Examiner*—Francisco C. Prats
*Attorney, Agent, or Firm*—Welsh & Katz, Ltd.

[57] ABSTRACT

A one-pot glycosylation reaction is disclosed in which a N-acetylgalactosamine (GalNAc) or N-acetylglucosamine (GlcNAc) group is enzymatically transferred to an acceptor molecule. The starting glycoside is a N-acetylamino monosaccharide 1-phosphate that is enzymatically converted to its UDP derivative via UTP and a pyrophorylase. The formed UDP derivative is epimerized, and the epimerized UDP derivative is used in the enzyme-catalyzed glycosyl transfer. That enzyme-catalyzed glycosyl transfer to an acceptor releases UDP that is enzymatically converted to UTP for further conversion of the N-acetylamino monosaccharide 1-phosphate into its UDP derivative.

4 Claims, No Drawings

N-ACETYLGALACTOSAMINYL OR N-ACETYLGLUCOSAMINYL TRANSFER USING N-ACETYLGLUCOSAMINYL-1-PHOSPHATE OR N-ACETYLGALACTOSAMINYL-1-PHOSPHATE AS PRECURSOR AND GLYCOSYL-NUCLEOTIDE REGENERATION

DESCRIPTION

This invention was made with government support under Contract No. GM 44154 awarded by the National Institutes of Health. The government has certain rights in the invention.

TECHNICAL FIELD

The present invention relates to glycosyl transfer in the synthesis of saccharide compounds, and more particularly to the single vessel enzyme-catalyzed transfer of an N-acetylgalactosaminyl or N-acetylglucosaminyl group to an acceptor using the epimeric N-acetylglucosaminyl-1-phosphate or N-acetylgalactosaminyl-1-phosphate, respectively, as the source of the transferred glycosyl group, with the regeneration of the corresponding UDP-glycoside.

BACKGROUND ART

The designed enzymatic synthesis of oligosaccharide-containing molecules has recently gained prominence in the art as greater numbers of glycosyl transferase enzymes have become available to skilled workers. See, for instance, U.S. Pat. Nos. 5,180,674 and 5,278,299. Indeed, two of the transferase enzymes discussed in U.S. Pat. No. 5,180,674 are an N-acetylgalactosamine transferase that transfers an N-acetylgalactosaminyl (GalNAc) group and an N-acetylglucosaminyl transferase that transfers an N-acetylglucosaminyl (GlcNAc) group.

The glycosyl groups GalNAc and GlcNAc are present alone and together in many naturally occurring oligosaccharide-containing compounds. For example, Beyer et al., *Adv. Enzymol.*, 52:23–175 (1981) report eight different types of linkages for GalNAc and seventeen for GlcNAc. Those compound types include not only oligosaccharides, but also glycoproteins and glycopeptides, proteoglycans, glycolipids and gangliosides.

The blood group antigens are exemplary of three important oligosaccharide compounds in which both glycosyl groups are present. For example, the non-reducing terminal groups of the A-blood group saccharides are GalNAcα1→3(Fucα1→2)Galβ-R', where R' is 1→3GlcNAc or 1→3GalNAc. The terminal saccharides of the O-blood group are Fucα(1→2)Galβ-R', whereas the B-blood group terminal saccharides are Galα(1→3)(Fucα1→2)Galβ-R' where each R' of the O- and B-blood groups is as above.

Each of GalNAc and GlcNAc is transferred to a specific acceptor by a transferase enzyme that recognizes the acceptor structure and the donor form of the glycosyl group. That donor form is a sugar nucleotide; i.e., UDP-GlcNAc or UDP-GalNAc.

Because the O-blood group antigen can be converted to the A-blood group antigen, the reactions of GalNAc and its transfer to a Fucα(1-2)Galβ-containing acceptor are among the most widely studied glycosyl transfer reactions. Indeed, U.S. Pat. No. 4,569,909 to Seno et al. teaches the use of uridine diphosphate-N-acetylglucosamine 4-epimerase to epimerize UDP-GlcNAc into an equilibrium mixture of UDP-GlcNAc and UDP-GalNAc. That mixture, after boiling to stop enzymic activity and centrifugation to remove the denatured enzyme, provided a "rough" preparation of UDP-GalNAc that was used with an α-N-acetylgalactosaminyl transferase referred to as "A-transferase" to convert Type O red blood cells into Type A red blood cells.

Seno et al. did not utilize the epimerase and transferase enzymes in the presence of each other. Seno et al. also began each of their reactions with UDP-GlcNAc, a compound that is relatively difficult to prepare and store in large quantity. Seno et al. also had no concept of a regeneration step in which UDP-GalNAc is recycled.

In addition to the blood group antigens, GlcNAc and GalNAc are present in several other important oligosaccharide compounds. For example, GlcNAc is present in both sialyl Lewis$^x$ (SLe$^x$) and sialyl Lewis$^a$ (SLe$^a$), both GlcNAc and GalNAc are present in the mucin oligosaccharides, and GalNAc is present as part of the T-antigen.

Thus, although the individual glycosyl transfer reactions of UDP-GalNAc and UDP-GlcNAc have been studied, as has the epimerization of UDP-GlcNAc to UDP-GalNAc and vice versa, the use of one or the other of GalNAc-1-phosphate and GlcNAc-1-phosphate as a starting material for the enzyme-catalyzed glycosyl transfer of the other saccharide to an acceptor, with regeneration of the UDP-glycoside in a one-pot system has not been taught except by the present inventor and colleagues in their recently published paper, Wong et al., *Pure & Appl. Chem.*, 65(4):803–808 (1993). The present invention provides such a system and provides a skilled worker with a UDP-glycosyl donor whose concentration is not controlled by the equilibrium position of the epimerase reaction.

BRIEF SUMMARY OF THE INVENTION

The present invention contemplates an enzymatic process for transferring a GalNAc or GlcNAc glycosyl group to an acceptor. The starting material for the transferred glycosyl group is its epimeric 1-phosphate. The contemplated process also recycles the UDP that is formed upon glycosyl transfer to form further amounts of UTP and thereby regenerate the UDP-glycoside.

In accordance with a preferred process, an aqueous reaction medium is formed by admixing the following ingredients in an aqueous medium in a single vessel:

(i) a monosaccharide phosphate that is one or the other of GalNAc-1-phosphate or GlcNAc-1-phosphate;

(ii) one or the other of UDP-GalNAc pyrophosphorylase or UDP-GlcNAc pyrophosphorylase that catalyzes the formation of UDP-GalNAc or UDP-GlcNAc from the monosaccharide phosphate of (i) in the presence of UTP;

(iii) a glycosyl transferase that is one or the other of a UDP-GalNAc or a UDP-GlcNAc transferase, the transferase present transferring whichever of GalNAc or GlcNAc is not present as the monosaccharide 1-phosphate of (i);

(iv) an epimerase that interconverts UDP-GalNAc and UDP-GlcNAc;

(v) an acceptor for the glycosyl transferase of (iii); and (vi) a uridine diphosphate recycling system that includes (a) UDP, UTP or both, (b) a phosphate donor, and (c) a kinase to transfer a phosphate group from the phosphate donor to UDP to form UTP. Each of the enzymes of (ii), (iii), (iv) and (vi) is present in a catalytic amount. The aqueous reaction medium so formed is maintained at a pH value of about 5 to about 10 at a temperature of about zero degrees C. to about 40° C. for a time period sufficient for said acceptor to be glycosylated. The glycosylated acceptor that is formed is preferably recovered.

ABBREVIATIONS

The various saccharides discussed herein are frequently discussed in their usually used abbreviations. Those abbreviations and saccharide names are listed below as monosaccharides.

Fuc=fucose
Gal=galactose
GalN=galactosamine
GalNAc=N-acetylgalactosamine
GalNAc-1-P=N-acetylgalactosamine 1-phosphate
Glc=glucose
GlcN=glucosamine
GlcN-1-P=glucosamine 1-phosphate
GlcN-6-P=glucosamine 6-phosphate
GlcNAc=N-acetylglucosamine
GlcNAc-1-P=N-acetylglucosamine 1-phosphate
GlcUA=glucuronic acid
IdUA=iduronic acid
Man=mannose

DETAILED DESCRIPTION OF THE INVENTION

The present invention contemplates an enzyme-catalyzed glycosyl transfer process in which a GlcNAc or GalNAc group is transferred to an acceptor by an appropriate glycosyl transferase. Both GalNAc and GlcNAc are transferred via their 1-UDP derivatives as the donor molecule that along with the acceptor is recognized by the glycosyl transferase. In accordance with one contemplated process, the source of the transferred glycosyl group is the epimeric monosaccharide 1-phosphate.

A contemplated process utilizes an aqueous reaction medium containing each enzyme and reactant in a single vessel (one-pot) to carry out a glycosyl transfer reaction. In accordance with a preferred process, an aqueous reaction medium is formed by admixing the following ingredients in a single vessel along with an aqueous buffer:

(i) a monosaccharide 1-phosphate that is one or the other of GalNAc-1-phosphate (GalNAc-1-P) or GlcNAc-1-phosphate (GlcNAc-1-P);

(ii) one or the other of UDP-GalNAc pyrophosphorylase or UDP-GlcNAc pyrophosphorylase that catalyzes the formation of UDP-GalNAc or UDP-GlcNAc from the monosaccharide 1-phosphate of (i) in the presence of UTP;

(iii) a glycosyl transferase that is one or the other of a UDP-GalNAc (GalNAc) or a UDP-GlcNAc (GlcNAc) transferase, the glycosyl transferase present in the aqueous reaction medium transferring whichever of GalNAc or GlcNAc that is not present as the monosaccharide 1-phosphate (i);

(iv) an epimerase that interconverts UDP-GalNAc and UDP-GlcNAc;

(v) an acceptor for the glycosyl transferase of (iii); and (vi) a uridine diphosphate recycling system that includes UDP, UTP or both, a phosphate donor, and a kinase to transfer a phosphate group from the phosphate donor to UDP to form UTP.

Each of the enzymes of (ii), (iii), (iv) and (vi) is present in a catalytic amount.

The aqueous reaction medium so formed is maintained at a pH value of about 5 to about 10 at a temperature of about zero degrees C. to about 40° C. and for a time sufficient for the acceptor to be glycosylated.

GalNAc-1-P and GlcNAc-1-P are both known compounds and can be obtained from any one of several literature preparations. Both materials are also available commercially from Sigma Chemical Co., St. Louis, Mo.

A particularly useful synthesis utilizes hexa-acetyl galactosamine or glucosamine as starting material. After reaction with a lipase or an amine such as butylamine in THF to remove the 1-position acetyl group, the resulting penta-acetate is reacted with a trivalent phosphitylating reagent such as dibenzyl N,N-diethylphosphoramidite in the presence of triazole or tetrazole in a dry solvent such as dichloromethane to form the corresponding 1-position dibenzyl phosphite. Oxidation of the phosphite with hydrogen peroxide or a similar oxidant provides the corresponding dibenzyl phosphate as the sodium salt. Hydrogenation over Pd/C followed by treatment with sodium hydroxide provides the desired phosphate. These reactions are discussed in PCT application WO 92/16640 published on Oct. 1, 1992 as well as in Ichikawa et al., *J. Org. Chem.*, 57:2943 (1992). A similar reaction is described in Martin et al., *Tet. Letters*, 3.3:6123–6126 (1992).

Heidlas et al., *J. Org. Chem.*, 57:146–151 (1992) also recently reported two syntheses of UDP-GlcNAc that each began with GlcN and GlcN-6-P. Both procedures started with GlcN that was cyclically phosphorylated to GlcN-6-P using ADP/ATP and acetyl phosphate in the presence of catalytic amounts of hexokinase (EC 2.7.1.1) and acetate kinase (EC 2.7.2.1).

In one process, GlcN-6-P was acetylated in THF/water using N-acetylsuccinimide (NAS) to form GlcNAc-6-P. Acetic anhydride can also be used. That N-acetyl compound was treated with an enzyme preparation from *Candida utilis* containing N-acetylglucosamine phosphomutase (EC 2.7.5.2) and UDP-GlcNAc pyrophosphorylase (EC 2.7.7.23) to first form GlcNAc-1-P and then UDP-GlcNAc in the presence of UTP and inorganic pyrophosphatase (EC 3.6.1.1) to destroy the inorganic pyrophosphate formed.

In the second process, GlcN-6-P was treated with phosphoglucomutase (EC 5.4.2.2) to form GlcN-1-P, which was then treated with UDP-Glc pyrophosphorylase (EC 2.7.7.9) in the presence of UTP to form UDP-GlcN. Inorganic pyrophosphate was removed as above. The UDP-GlcN was then acetylated with NAS as above to form UDP-GlcNAc, although acetic anhydride can also be used here.

The above first process disclosed by Heidlas et al. can be used herein for in situ preparation of GlcNAc-1-P after the acetylation step. One can thus start with GlcNAc-6-P rather than GlcNAc-1-P, as the former compound can be converted into the latter using the *Candida utilis* preparation.

A pyrophosphorylase that forms UDP-GlcNAc or UDP-GalNAc from UTP and the monosaccharide 1-phosphate is also present in the aqueous reaction medium. Where GlcNAc-1-P is present as the starting material, UDP-GlcNAc pyrophosphorylase is used. Where GalNAc-1-P is present as the starting material, UDP-GalNAc pyrophosphorylase is used.

The before-mentioned Seno et al. U.S. Pat. No. 4,569,909 teaches the addition of sodium pyrophosphate and UDP- GlcNAc pyrophosphorylase to a formed equilibrium mixture of UDP-GlcNAc and UDP-GalNAc to decompose UDP-GlcNAc. That addition was made after the boiling step that deactivates and precipitates the epimerase enzyme, as loss of UDP-GlcNAc while the epimerase is present and active would reverse the equilibrium and remove desired UDP-GalNAc.

In the present process, there is no pyrophosphate added, and the pyrophosphorylase is used in recycling the UDP/UTP to make more UDP-GalNAc or UDP-GlcNAc, rather than decompose the UDP-saccharide. Here, also, the active pyrophosphorylase is present in the same solution (aqueous reaction medium) as the active epimerase.

UDP-GlcNAc and UDP-GalNAc pyrophosphorylase enzymes are well known and can be readily obtained by published procedures. For example, Seno et al. U.S. Pat. No. 4,569,909 teaches that UDP-GlcNAc pyrophosphorylase can be obtained from *Staphylococcus aureus* or baker's yeast (*Saccharomyces cerevisiae*). The Whitesides research group reported using a preparation from *Candida utilis* (Torula yeast) for UDP-GlcNAc pyrophosphorylase (EC 2.7.7.23) [Heidlas et al. *J. Org. Chem.*, 57:146–151 (1992), and the citations therein]. Maley et al., *Biochem. J.*, 107:637–644 (1968) report a UDP-GalNAc pyrophosphorylase in a rat liver extract they prepared.

The glycosyl transferase used is specific for both the transferred glycosyl group and the acceptor to which the glycosyl group (GalNAc or GlcNAc) is transferred. The transferase enzymes that form naturally occurring saccharide linkages are known and have been isolated. Several of these enzymes are noted with citations in Beyer et al., *Adv. Enzymol.*, 52:23–175 (1981), with additional enzymes being described by Hindsgaul and co-workers in Srivastava et al., *Carbohyd. Res.*, 207:259–276 (1990) and in Hindsgaul et al., *J. Biol. Chem.*, 266(27):17858–17862 (1991); and in Ropp et al., *J. Biol. Chem.*, 266:23863 (1991); and van Halbeek et al., *Eur. J. Biochem.*, 127:21 (1992). See, also, Wong et al., *J. Biol. Chem.*, 267:12709–12716 (1992) and Briand et al., *J. Biol. Chem.*, 156:12205–12207 (1981) and the citations therein for peptide-glycosylating enzymes. A still further compilation of these transferases, their common names and some of their EC designations is provided in Brockhausen, *Crit. Rev. Clin. Lab. Sci.*, 39(2):65–151 (1993), and the citations therein. A particular glycosyl transferase desired can be prepared as discussed in the above papers, and need not be purified as whole cells and cell extracts can be utilized.

It is to be understood that the glycosyl transferase utilized in the aqueous reaction medium in a preferred embodiment is an enzyme that transfers a GalNAc group where GlcNAc-1-P is the monosaccharide phosphate, or transfers a GlcNAc group where GalNAc-1-P is the monosaccharide phosphate of the aqueous reaction medium. Thus, the glycosyl transferase present in the aqueous reaction medium preferably transfers whichever of GalNAc or GlcNAc is not present as the monosaccharide phosphate of the aqueous reaction medium.

An enzyme that can interconvert UDP-GalNAc and UDP-GlcNAc is also present. This enzyme can be referred to as a UDP-GlcNAc/UDP-GalNAc epimerase to indicate which ring position is epimerized. Enzymes from several sources are reported in the literature.

It is emphasized that the same enzyme can be used regardless of whether a GalNAc or GlcNAc is transferred. This is because one of those epimerization products is constantly removed from the equilibrium by the glycosyl transfer thereby causing more of that product to be formed.

UDP-GlcNAc 4-epimerase is one exemplary enzyme, and it can be prepared from *Bacillus subtilis* strains IFO 3007 and IFO 3009 (IFO=Institute for Fermentation, Osaka, Japan), as noted in Seno et al. U.S. Pat. No. 4,569,909. That patent teaches making of a cell-free extract enzyme preparation using ammonium sulfate fractionation of ruptured cells.

That UDP-GlcNAc 4-epimerase converts UDP-GalNAc to UDP-GlcNAc and vice versa. The equilibrium between the two UDP derivative forms provides the two UDP derivatives in about a 2:1 molar ratio favoring UDP-GlcNAc, according to Seno et al. Thus, starting with GalNAc-1-P that is converted here into UDP-GalNAc, the equilibrium for this enzyme favors production of UDP-GlcNAc. On the other hand, starting with GlcNAc-1-P, the transfer of GalNAc would appear to be disfavored, particularly if the active epimerase is not present along with active glycosyl transferase. However, because an active epimerase and a UDP-GalNAc transferase are present, the reaction proceeds.

Another exemplary useful UDP-GalNAc 4-epimerase was reported by Maley et al., *Biochem. J.*, 107:637–644 (1968). The equilibrium with this enzyme lies toward UDP-GlcNAc, with a molar ratio of about 7:3. See also, Maley et al., *Biochim. Biophys. Acta*, 31:557–563 (1959).

One of the benefits of the present invention is that by utilizing UDP-GalNAc transferase in the presence of active UDP-GlcNAc/UDP-GalNAc epimerase, the UDP-GalNAc produced by the enzymatic epimerization equilibrium can be constantly used via glycosyl transfer so that the position of the equilibrium is of little consequence. Thus, the yield of GalNAc-containing product can be increased over that expected if the equilibrium is established and the epimerase activity is eliminated by boiling as taught by Seno et al. The same, of course, holds true where UDP-GlcNAc transferase is present for that glycosyl transfer.

Still further, as noted before, the presence in the reaction medium of UDP-GlcNAc pyrophosphorylase (or UDP-GalNAc pyrophosphorylase) in the presence of an active epimerase and active glycosyl transferase continually makes more UDP-GlcNAc (UDP-GalNAc) from GlcNAc-1-P (GalNAc-1-P) so that as the transferase uses up the UDP-GalNAc (UDP-GlcNAc) made by the epimerase, more UDP-GlcNAc (UDP-GalNAc) is made, making still more UDP-GalNAc (UDP-GlcNAc) available for transfer.

The acceptor utilized can be any of a wide variety of oligosaccharides, proteins, peptides, glycoproteins or glycopeptides. The choice of a particular acceptor is governed by the choice of whether GalNAc or GlcNAc is to be transferred and the transferase employed. In most instances, glycosyl transferase specificity is determined by the non-reducing terminal saccharide alone or in conjunction with about one to about four adjacent saccharides. Thus, once the skilled worker has provided an acceptor having the structural requirements for a given transferase to be used, the remaining saccharide or other constituent groups toward the reducing terminus of a saccharide-containing acceptor are not relevant to the transfer reaction, so long as the acceptor possesses minimal solubility in the aqueous reaction medium to be acted upon by the transferase. Similarly, amino acid residues on either side of a serine/threonine or an asparagine of a peptide or protein do not appear to play a role in the selectivity of glycosylation.

Exemplary non-reducing terminal structures formed by reaction of various acceptors with the several UDP-GalNAc and UDP-GlcNAc transferases are noted in the before-discussed Beyer et al., *Adv. Enzymol.*, 52:23–175 (1981) and Brockhausen, *Crit. Rev. Clin. Lab. Sci.*, 30(2):65–151

(1993) reviews and are shown below in Tables 1 and 2 along with common names and EC designations for several of those enzymes:

TABLE 1

UDP-GalNAc Transferases

| Structure | EC Designation | Common Name |
|---|---|---|
| GalNAcα1→3(Fucα1→2)Galβ- | 2.4.1.40 | blood group A α3-GalNAc-T |
| GalNAcα1→Ser/Thr | 2.4.1.41 | polypeptide α-GalNAc-T |
| GalNAcβ1→4Gal | | blood group Cad or $S^d$ β4-GalNAc-T |
| GalNAcβ1→3Gal | | Core 5α3-GalNAc-T |
| GalNAcα1→3GalNAc | — | — |
| (GalNAcβ1→4GlucUAβ1→3-)$_n$ | — | — |
| (GalNAcβ1→4IdUAα1→3-)$_n$ | — | — |

TABLE 2

UDP-GlcNAc Transferases

| Structure | EC Designation | Common Name |
|---|---|---|
| GlcNAcβ1→4GlcNAc | 2.4.1.119 | Oligosaccharyl-T |
| GlcNAcβ1→Asn | — | — |
| GlcNAcβ1→2Man | 2.4.1.101 | GlcNAc-T I |
| | 2.4.1.143 | GlcNAc-T II |
| GlcNAcβ1→4Man | 2.4.1.144 | GlcNAc-T III |
| | 2.4.2.145 | GlcNAc-T IV |
| | — | GlcNAc-T VI |
| GlcNAcβ1→6Man | 2.4.1.155 | GlcNAc-T V |
| GlcNAcβ1→3Man | — | — |
| GlcNAcα1→3Man | — | — |
| GlcNAcβ1→3Gal | 2.4.1.149 | blood group i β3-GlcNAc-T |
| | 2.4.1.146 | elongation β3-GlcNAc-T |
| GlcNAcβ1→4Gal | — | — |
| GlcNAcβ1→6Gal | 2.4.1.150 | blood group I β6-GlcNAc-T |
| GlcNAcα1→4Gal | — | — |
| GlcNAcα1→4GlcNAc | — | — |
| GlcNAcβ1→6GalNAc | 2.4.1.102 | core 2 β6-GlcNAc-T |
| | 2.4.1.148 | core 4 β6-GlcNAc-T |
| GlcNAcβ1→3GalNAc | 2.4.1.147 | core 3 β3-GlcNAc-T |
| GlcNAcβ1→4GalNAc | — | — |
| GlcNAcα1→4GlcUA | — | — |
| GlcNAcα1→4IdUA | — | — |

The final component in the aqueous reaction medium is a uridine diphosphate/uridine triphosphate (UDP/UTP) recycling (regenerating) system. This system recycles UDP that is formed upon glycosyl transfer from UDP-GalNAc or UDP-GlcNAc to the acceptor, regenerates UTP, and that regeneration is used to form more UDP-GlcNAc or UDP-GalNAc that can be epimerized and then transferred. The UDP/UTP recycling or regenerating system contains three basic ingredients: (a) UDP, UTP or both, (b) a phosphate donor, and (c) a kinase to transfer a phosphate group from the phosphate donor to UDP.

Either or both of UDP and UTP can be present inasmuch as UDP is converted into UTP, and after the glycosyl transfer reaction, UDP is formed again. Because UDP and UTP interconvert and are reused, the total amount of one or the other is usually discussed rather than amounts for both.

The phosphate donor of the regenerating system is a phosphorylated compound, the phosphate group of which can be used to phosphorylate UDP to form UTP. The only limitation on the selection of a phosphate donor is that neither the phosphorylated nor the dephosphorylated forms of the phosphate donor substantially interferes with any of the reactions involved in the formation of the glycosylated acceptor saccharide. Preferred phosphate donors are phosphoenolpyruvate (PEP) and acetyl phosphate (AcOP). A particularly preferred phosphate donor is PEP, which forms pyruvate (PYR) after phosphate transfer.

The selection of a particular kinase for use in accordance with the present invention depends upon the phosphate donor employed. When acetyl phosphate is used as the phosphate donor, the kinase is acetate kinase (EC 2.7.2.1). When PEP is used as the phosphate donor, the kinase is pyruvate kinase (PK; EC 2.7.1.40). Other kinases can be employed with other phosphate donors as is well known to those of skill in the art. Kinases are commercially available (Sigma Chem. Co., St. Louis, Mo.; Boehringer Mannheim, Indianapolis, Ind.).

Each of the enzymes utilized in the above process is present in a catalytic amount as is discussed further hereinafter.

The enzyme-catalyzed formation of a UDP-glycoside from an N-acetylamino monosaccharide 1-phosphate and UTP also generates inorganic pyrophosphate. In one preferred embodiment, the inorganic pyrophosphate (PPi) formed is enzymatically decomposed to inorganic phosphate (Pi) by inorganic pyrophosphatase (PPase; EC 3.6.1.1) that can also be present in the aqueous reaction mixture in a catalytic amount. The presence of PPi in the aqueous reaction mixture can inhibit some of the enzymes.

A schematic diagram of a process of the invention is illustrated below in Scheme 1, and shows glycosyl transfer by both UDP-GalNAc and UDP-GlcNAc for completeness. In that scheme, the acceptor for both transfers is shown generically as R—OH, with the understanding that transfer to an asparagine residue is also contemplated. Six enzymes that can be present are denoted E1–E6, and are identified below the scheme. PPase is not shown for greater clarity. The longer arrow toward UDP-GlcNAc for E6, the epimerase, indicates that the equilibrium lies toward UDP-GlcNAc.

It is to further understood that only four of those six enzymes are present in a preferred process. Thus, where GlcNAc-1-P is the starting material, E4 (UDP-GalNAc pyrophosphorylase) is absent from the aqueous reaction medium, as is E2 (GlcNAc transferase). Similarly, where GalNAc-1-P is the starting material, E5 (UDP-GlcNAc pyrophosphorylase) and E1 (GalNAc transferase) are absent from the aqueous reaction medium.

Scheme 1

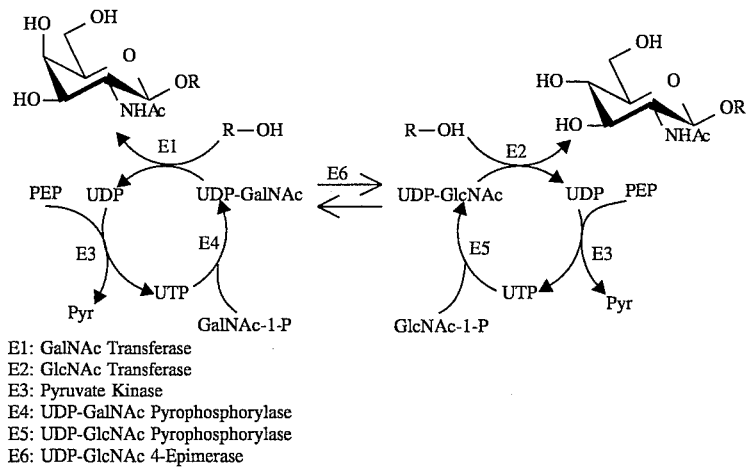

E1: GalNAc Transferase
E2: GlcNAc Transferase
E3: Pyruvate Kinase
E4: UDP-GalNAc Pyrophosphorylase
E5: UDP-GlcNAc Pyrophosphorylase
E6: UDP-GlcNAc 4-Epimerase Schemes 1A and 1B, hereinafter, are dissected forms of Scheme 1 that separately illustrate the reaction and the above-discussed materials present in the aqueous reaction medium for each of the two processes contemplated. Again, the PPi formed by the pyrophosphorylase-catalyzed reactions is not shown, nor is its decomposition by PPase illustrated.

Thus, in Scheme 1A, GlcNAc-1-P is formed into UDP-GlcNAc by E5, UDP-GlcNAc pyrophosphorylase, reacting with UTP, with release of PPi. UDP-GlcNAc is epimerized by E6, UDP-GlcNAc/UDP-GalNAc epimerase, to form UDP-GalNAc that reacts with the acceptor, R—OH, in the presence of E1, GalNAc transferase, to form the glycosylated product and UDP. That formed UDP is the UDP that is shown on the right side of the scheme that is recycled via E3, pyruvate kinase, and PEP to form UTP. That UTP reacts with more GlcNAc-1-P via E5 to form more UDP-GlcNAc so more GalNAc-containing product can be formed.

Scheme 1B shows the second contemplated process that begins with GalNAc-1-P that is used to form a product that is glycosylated with a GlcNAc group via E2, GlcNAc transferase. GalNAc-1-P is formed into UDP-GalNAc by reaction with UTP in the presence of E4, UDP-GalNAc pyrophosphorylase, with release of PPi. The recycling or regeneration steps with UDP and UTP are the same as those discussed above, with the epimerization with E6 forming UDP-GlcNAc that is formed is utilized in the transferase-catalyzed reaction with E2.

It should also be understood that glycosyl transfer of GalNAc can be accomplished beginning with GalNAc-1-P and that a similar transfer can be accomplished for GlcNAc beginning with GlcNAc-1-P. Thus, the epimerase shown as E6 in Scheme 1, above, and Schemes 1A and 1B, below, need not be present in some embodiments, and the transferase used transfers the GlcNAc or GalNAc group without epimerization. However, preferred glycosylation reactions include the epimerase and are exemplified by either of Schemes 1A or 1B, below.

Scheme 1A

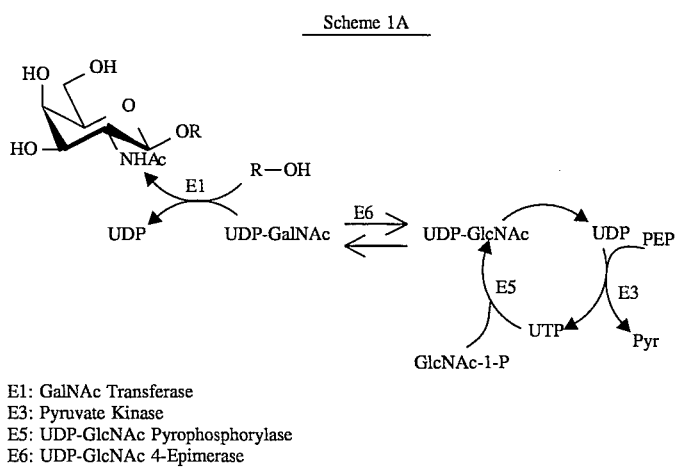

E1: GalNAc Transferase
E3: Pyruvate Kinase
E5: UDP-GlcNAc Pyrophosphorylase
E6: UDP-GlcNAc 4-Epimerase Scheme 1B

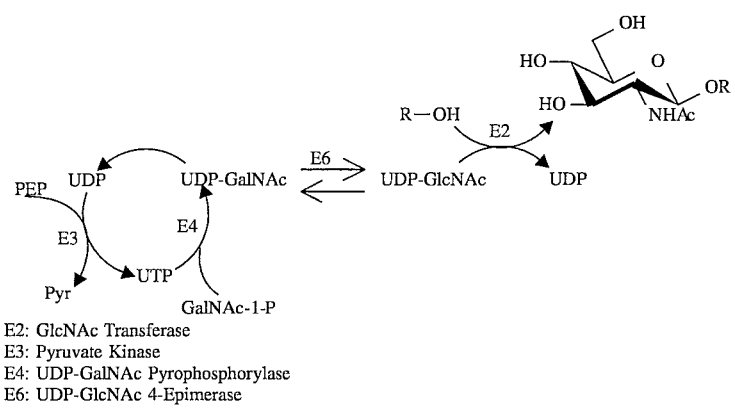

E2: GlcNAc Transferase
E3: Pyruvate Kinase
E4: UDP-GalNAc Pyrophosphorylase
E6: UDP-GlcNAc 4-Epimerase As used herein, the phrase "catalytic amount" means that amount of an enzyme at least sufficient to catalyze, in a non-rate limiting manner, the conversion of that enzyme's substrate to product. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

Admixing comprises mixing each ingredient with each of the other ingredients in a suitable aqueous buffer medium (solvent) to form a reaction mixture or aqueous reaction medium. The aqueous reaction medium is preferably a solution or dispersion of the various components. It is also preferred that the enzymes used be free and not bound to solid supports. Thus, in preferred practice, the aqueous reaction medium is substantially homogeneous.

The temperature utilized can range from about zero degrees C. to the temperature at which the first enzyme denatures, as is readily determined. The process is usually carried out at a temperature of 15° C. to about 40° C. Preferably temperature is from about 20° C. to about 40° C. and, more preferably from about 25° C. to about 37° C. Ambient atmospheric pressure is also preferably utilized.

The pH value can range from about 5.0 to about 10.0. Preferably, the pH value is from about 6.5 to about 8.5 and, more preferably about 7.0 to about 7.5. The pH value is maintained by buffers in the aqueous solvent. The buffer is free of chelators that bind enzyme cofactors such as $Mg^{+2}$ or $Mn^{+2}$ and effectively remove them from the aqueous reaction medium. A chelator such as EDTA can be and preferably is present.

The selection of a buffer is based on the ability of the buffer to maintain pH value at the desired level. Where the pH value is about 7.5, a useful buffer is HEPES. Where the pH value is about 7.0–9.0, tris-HCl can also be used.

The osmolality and ionic composition of the aqueous solvent medium are designed and selected to solubilize the ingredients of the reaction mixture in active form, and to provide cofactors for the enzymes contained in the reaction mixture. The osmolality of the aqueous solvent including the buffer is preferably from about 100 mOsm to about 300 mOsm.

Minor amounts (e.g. up to about 10 percent by volume) of organic solvents that do not substantially inhibit the reaction can also be present to augment solubility of the acceptor. Exemplary solvents include DMSO, THF and acetonitrile. Solubilizing detergents such as Triton X-100, octyl-beta-D-glucopyranoside (Calbiochem), MEGA-8-9 or -10 (Calbiochem), CHAPS or CHAPSO (Calbiochem) or Tween-20 that do not denature the enzymes can also be present to improve solubility of the enzymes and acceptor, although it is preferred that the aqueous reaction medium be free of such detergents.

The reaction time and conditions for the glycosylation reaction vary with several parameters such as pH value, the reaction temperature, components of the reactions, their amounts, and the amount of glycosylation desired. Typical reaction times at ambient room temperature (e.g. about 22° C.) range from about one hour where only minimal reaction is desired to about three to about five days, where substantial consumption of the acceptor and resulting product formation is desired.

The concentration or amount of the various reactants used in a contemplated glycosylation process depend upon numerous factors including reaction conditions such as temperature and pH value, and the amount of acceptor to be glycosylated. Because this glycosylation process utilizes regeneration of UDP in the presence of catalytic amounts of the enzymes, the method is limited by the concentrations or amounts of monosaccharide 1-phosphate, phosphate donor and acceptor. The upper limit for the concentrations of reactants that can be used in accordance with the method of the present invention is determined by the solubility of those reactants.

In a preferred embodiment, glycosylation is limited by the concentration of the starting monosaccharide 1-phosphate, or its precursor when that monosaccharide 1-phosphate is made in situ. According to such an embodiment, the concentrations of total UDP, phosphate donor, acceptor and enzymes are selected such that glycosylation proceeds until the starting monosaccharide 1-phosphates is substantially consumed.

By way of example, when the concentration of GalNAc-1-P or GlcNAc-1-P is about 50 mM, preferred concentrations of the other non-enzyme reactants are about 50 mM for the acceptor, about 500 μM for total UDP, and about 50 mM for the phosphate donor. The ratio of the concentration of these reactants to the concentration of monosaccharide phosphate is preferably about 0.9–1.2:1 for the acceptor, about 50–100:1 for UDP and about 1.0–1.2:1 for the phosphate donor.

The glycosylation process further preferably comprises isolating or recovering the glycosylated acceptor. Isolation comprises recovering the glycosylated acceptor from the reaction mixture. Means for recovering the glycosylated acceptor include gel filtration, column chromatography, paper chromatography, affinity chromatography, extraction, precipitation and the like, as are well known.

In a preferred embodiment, isolation and recovery are accomplished by lyophilizing the reaction mixture to reduce the volume of the reaction mixture, applying the lyophilized reaction mixture to a gel filtration column of about 200–400 mesh and eluting the glycosylated acceptor compound from the filtration column. The glycosylated acceptor can then be further purified and isolated using usual, well known techniques.

It is to be understood that the glycosylated acceptor need not be isolated (recovered) but can be used in another synthetic step in the aqueous reaction mixture or in another reaction mixture from which the glycosylated acceptor product was not itself previously recovered. For example, where a contemplated process is utilized to add a GlcNAc to Man-containing compound as with the GlcNAc transferase enzyme GlcNAcT-III (EC 2.4.1.144) to form a GlcNAc$\beta$1→4Mam linkage, it can be advantageous to add a further Gal to the non-reducing terminal GlcNAc moiety to form a compound containing the structure Gal$\beta$1→4GlcNAc$\beta$1→4Man. To do so, UDP-Gal and $\beta$1→4galactosyl transferase need only be added to the reaction mixture to prepare the desired derivative.

In other embodiments, it can be useful to denature and separate the enzymes from the other materials present in the aqueous reaction medium and then add the ingredients required for the next step. This denaturization and separation can be effected by boiling the aqueous reaction medium for a time sufficient to denature the enzymes, e.g. about 5–10 minutes, followed by centrifugation and separation of the resulting precipitate from the supernatant. The supernatant is then used for the next reaction as noted above.

EXAMPLES

EXAMPLE 1

Synthesis of Mucin-Type Oligosaccharide

The reducing terminal portion of mucin-type oligosaccharides contain the oligosaccharide group Fuc$\alpha$1→2Gal$\beta$1→3($\beta$1→6GlcNAc)GalNAc, Compound 1. That oligosaccharide is $\alpha$-bonded to a serine or threonine in native mucin.

An aqueous medium is prepared that contains GalNAc-1-P (25 mg, 73 $\mu$mol), UDP (35 mg, 73 $\mu$mol), PEP Na$_3$ salt (20 mg, 85 $\mu$mol), EDTA (3 mM), and MgCl$_2$ (5 mM) in HEPES buffer (100 mM, 5 mL) and is adjusted to a pH value of 7.5 with NaOH. Freeze-dried bakers' yeast cells (50 mg) and pyruvate kinase (PK; 200 U) are added to the aqueous medium and the resulting admixture is stirred for about 10 hours at 23° C. under an argon atmosphere. The yeast cells provide a ready source of UDP-GalNAc pyrophorylase.

After UDP-GalNAc is observed, as evidenced by thin layer chromatography (TLC; iP$_2$OH/H$_2$O/NH$_4$OH; 7:3:1 v/v), Compound 2 [Gal$\beta$1→3GalNAc; prepared as described in Look et al., *J. Org. Chem.*, 58 (15) :4326–4330 (1993)], (10 mg, 26 mmol), leupeptin (0.5 mg/mL), pepstatin (0.7 mg/mL), Tween 20 (50 $\mu$L), dithiothreitol (3.8 mg), phenylmethylsulfonyl fluoride (PMSF) (0.2 mM), UDP-GalNAc 4-epimerase [Look et al., *J. Org. Chem.*, 58(15):4326–4330 (1993)] and a crude cell extract containing UDP-GlcNAc$\beta$1→6 transferase [Ropp et al., *J. Biol. Chem.*, 266:23863 (1991); van Halbeek et al., *Eur. J. Biochem.*, 127:21 (1982)] are added to the aqueous medium to form an aqueous reaction medium. The aqueous reaction medium so formed is maintained for two days at room temperature under an argon atmosphere, concentrated, and chromatographed on silica gel (ETOAc/AcOH/H$_2$O, 3:2:1 v/v) followed by Bio Gel P-2 filtration with water to obtain Compound 3, Gal$\beta$1→3(1→6GlcNAc)GalNAc, after lyophilization as a mixture of anomers.

Compound 3 is reacted as described in Hindsgaul et al., *J. Biol. Chem.*, 266(27): 17858–17862 (1991) using $\alpha$(1→2)fucosyltransferase (EC 2.4.1.69) in a scaled-up synthesis without the radiolabeled GDP-fucose and the inhibitor used in that paper. The reaction mixture utilizes Compound 3, GDP-Fuc, MnCl$_2$, ATP and the $\alpha$(1→2)fucosyltransferase in a tris buffer containing NaN$_3$ at pH 7.0 to form Compound 1.

It should be apparent that Compound 3 can also be formed as discussed above, by starting with GlcNAc-1-P, eliminating the epimerase, and replacing the bakers' yeast cells with a UDP-GlcNAc pyrophorylase-containing preparation from *C. utilis*. Compound 1 is then prepared as discussed before.

It should also be apparent that Compound 20, GlcNAc1→3(Fuc$\alpha$1→2)Gal$\beta$1→3GalNAc, can be prepared by replacing the UDP-GlcNAc$\beta$1→6 transferase with elongation $\beta$-3-GlcNAc-T (EC 2.4.1.146) in the aqueous reaction medium to form GlcNAc$\beta$1→3Gal$\beta$1→3GalNAc (Compound 21), followed by the above fucosylation.

EXAMPLE 2

Synthesis of Blood Type-A Antigen

The blood Group H antigen, Compound 4, has the structure Fuc$\alpha$1→2Gal$\beta$1→4GlcNAc and can be prepared from N-acetyllactosamine using GDP-Fuc and $\alpha$(1→2)fucosyltransferase (EC 2.4.1.69) as discussed above. Addition of a GalNAc group to the 3-position of the non-reducing terminal saccharide (Gal) transforms the H antigen into the Type-A antigen, GalNAc$\alpha$1→3(Fuc$\alpha$1→2)Gal$\beta$1→4GlcNAc, Compound 5.

A reaction medium similar to that discussed in Example 1 is provided except that GlcNAc-1-P is substituted for GalNAc-1-P and a UDP-GlcNAc pyrophosphorylase-containing preparation from *C. utilis* and a UDP-GlcNAc 4-epimerase-containing preparation as described in Maley et al., *Biochem. J.*, 107:637–644 (1968) are substituted for the bakers' yeast preparation.

After UDP-GlcNAc is observed by TLC as before, an aqueous medium is prepared as in Example 1 by substituting Compound 4 for Compound 2 and substituting (fucosyl $\alpha$1→2)galactoside $\alpha$1→3 N-acetylgalactosaminyltransferase (EC 2.4.1.40) for the UDP-GlcNAc transferase of Example 1. This enzyme has been isolated from various sources including porcine gastric mucosa, porcine and human submaxillary glands, human milk, human gastric mucosa, human serum and other sources as discussed in Beyer et al., *Adv. Enzymol.*, 52:23–175, 68–70 (1981).

The aqueous reaction medium so formed is maintained for two days under an argon atmosphere. The desired material, Compound 5 is obtained as a mixture of anomers as discussed in Example 1.

Following the discussion Example 1, it should be apparent Compound 5 can also be formed from Compound 4 by stating with GalNAc-1-P, eliminating the epimerase preparation, and using the bakers' yeast preparation of the pyrophorylase of Example 1 instead of the *C. utilis* preparation.

EXAMPLE 3

Sialyl Lewis X Analogue

Sialyl Lewis X (SLe$^x$) has the structure NeuAcα2→3Galβ1→4(Fucα1→3)GlcNAc, and is a carbohydrate that can inhibit E-selectin-mediated adhesion. Tyrell et al., *Proc. Natl. Acad. Sci. USA*, 88.:10372–10376 (1991). Compound 6, NeuAcα2→3Galβ1→4(Fucα1→3)-GlcNAcβ1→4GlcNAc-OCH$_3$, is an analogue of SLe$^x$ that can inhibit the binding (adhesion) of neutrophils to the E-selectin receptor.

An aqueous medium containing GalNAc-1-P similar to that of Example 1 is prepared. After UDP-GalNAc is observed by TLC, an aqueous reaction medium similar to that prepared in Example 1, with two exceptions, is prepared. Those exceptions are (1) that the UDP-GlcNAcβ1→6 transferase of Example 1 is replaced by the UDP-GlcNAcβ1→4 transferase prepared as described in Leloir et al., *Biochem. Biophys. Res. Commun.*, 52:1285–1292 (1973) (EC 2.4.1.119), and (2) the acceptor compound is GlcNAc-OCH$_3$ instead of Compound 2.

The aqueous reaction medium is maintained at room temperature under an argon atmosphere for two days. The GlcNAcβ1→4GlcNAc-OCH$_3$, Compound 7, resulting from that reaction can then be obtained chromatographically. Compound 7 can also be formed directly using GlcNAc-1-P, no epimerase and the appropriate pyrophosphorylase, as discussed in Example 2.

The trisaccharide Galβ1→4GlcNAcβ1→4GlcNAc-OCH$_3$, Compound 8, can be prepared from Compound 7 following the cyclic galactosyl transfer reaction described in Wong et al., *J. Org. Chem.*, 47:5416–5418 (1982) using GlcNAcβ1→4 galactosyl transferase (EC 2.4.1.22).

Sialylation of Compound 8 using the cyclic process described in allowed U.S. application Ser. No. 07/670,701, filed Mar. 18, 1991, now U.S. Pat. No. 5,278,299, provides NeuAcα2–3Galβ1→4GlcNAcβ1→4GlcNAc-OCH$_3$, Compound 9. A particularly useful sialyltransferase for use in that process is the recombinant enzyme described by the Paulson group in Wen et al., *J. Biol, Chem.*, 267 (29) :21011–21019 (1992) .

Fucosylation of Compound 9 with α1,3 fucosyl transferase (EC 2.4.1.152) or α1,¾ fucosyl transferase (EC 2.4.1.65) as discussed in Dumas et al., *Bioorg. Med. Chem. Lett.*, 1:425 (1991) or Wong et al., *J. Am. Chem. Soc.*, 114:7321 (1992), respectively, provides the desired SLe$^x$ analogue, Compound 6.

EXAMPLE 4

Sialyl Lewis A Analogue

Sialyl Lewis A (SLe$^a$) is another ligand that inhibits E-selectin-mediated adhesion. The position of the Gal and Fuc groups are switched in SLe$^a$ relative to those in SLe$^x$. A SLe$^a$ analogue, Compound 10, is represented by the structure NeuAcα2→3Galβ1→3(Fucα1→4)GlcNAcβ1→4GlcNAc-OCH$_3$.

Compound 10 is prepared in the same manner as Compound 6, except that the GlcNAcβ1→3 galactosyl transferase described by Basu et al., *Fed. Proc.*, 30:1133–1135 (1971) is used in place of the GlcNAcβ1→4 galactosyl transferase used in Example 3, and the fucosylα1→¾ transferase noted in Example 3 is utilized.

Thus, Compound 7 of Example 3 is prepared by either procedure, and a Gal group is added to the non-reducing terminus using the galactosyl transferase of Basu et al., above, to form Compound 11, Galβ1→3GlcNAcβ1→4GlcNAc-OCH$_3$. Compound 11 is sialylated as in Example 3 to form Compound 12, NeuAcα2→3Galβ1→3GlcNAcβ1→4GlcNAc-OCH$_3$. Compound 12 is then fucosylated as described in Wong et al., *J. Am. Chem. Soc.*, 114:732 (1992) using the α1→¾ fucosyl transferase to form SLe$^a$ analogue Compound 10.

The foregoing description and the examples are intended as illustrative and are not to be taken as limiting. Still other variations within the spirit and scope of this invention are possible and will readily present themselves to those skilled in the art.

What is claimed is:

1. A process for using N-acetylgalactosamine 1-phosphate (GalNAc-1-P) or N-acetylglucosamine 1-phosphate (GlcNAc-1-P), respectively, to glycosylate an acceptor with GlcNAc or GalNAc, respectively, with recycling of uridine diphosphate that comprises the steps of:

(a) admixing the following ingredients in an aqueous medium within a single vessel to form an aqueous reaction medium (i) a monosaccharide phosphate that is one or the other of GalNAc-1-phosphate or GlcNAc-1-phosphate;

(ii) one or the other of UDP-GalNAc pyrophosphorylase or UDP-GlcNAc pyrophosphorylase that catalyzes the formation of UDP-GalNAc or UDP-GlcNAc from the monosaccharide phosphate of (i) in the presence of UTP;

(iii) a glycosyl transferase that is one or the other of a GalNAc or a GlcNAc transferase, the transferase present transferring whichever of GalNAc or GlcNAc is not present as the monosaccharide 1-phosphate of (i);

(iv) an epimerase that interconverts UDP-GalNAc and UDP-GlcNAc;

(v) an acceptor for the glycosyl transferase of (iii); and (vi) a uridine diphosphate recycling system that includes (a) UDP, UTP or both, (b) a phosphate donor, and (c) a kinase to transfer a phosphate group from the phosphate donor to UDP to form UTP, wherein each of the enzymes of (ii), (iii), (iv) and (vi) is present in a catalytic amount; and (b) maintaining said aqueous reaction medium at a pH value of about 5 to about 10 at a temperature of about zero degrees C. to about 40° C. for a time period sufficient for said acceptor to be glycosylated.

2. The process according to claim 1 including the further step of recovering the glycosylated acceptor.

3. The process according to claim 1 wherein said monosaccharide phosphate is GalNAc-1-phosphate.

4. The process according to claim 1 wherein said monosaccharide phosphate is GlcNAc-1-phosphate.

* * * * *